(12) United States Patent
Olshenitsky et al.

(10) Patent No.: US 6,569,424 B2
(45) Date of Patent: May 27, 2003

(54) BACTERIAL STRAIN, PROCESSES PLANT EXTRACTS, COMPOSITIONS CONTAINING SAME, PROCESSES FOR THEIR PREPARATION AND THEIR THERAPEUTIC AND INDUSTRIAL APPLICATIONS

(75) Inventors: Mark Olshenitsky, Natania (IL); Genadi Buchman, Bat Yam (IL)

(73) Assignee: The Bio Balance Corporation, New York, NY (US)

( * ) Notice: Subject to any disclaimer, the term of this patent is extended or adjusted under 35 U.S.C. 154(b) by 0 days.

(21) Appl. No.: 09/986,861

(22) Filed: Nov. 13, 2001

(65) Prior Publication Data

US 2002/0054868 A1 May 9, 2002

Related U.S. Application Data

(60) Division of application No. 09/725,846, filed on Nov. 30, 2000, which is a continuation-in-part of application No. PCT/IL00/00318, filed on Jun. 1, 2000.

(51) Int. Cl.$^7$ ........................ A01N 63/00; A61K 35/78; B09B 3/00

(52) U.S. Cl. ...................... 424/93.3; 424/725; 424/736; 424/773; 424/774; 424/775; 424/776; 424/777; 424/778; 424/779; 426/531; 426/541; 426/542; 426/599; 426/615; 426/616; 426/623; 426/629; 426/630; 426/635; 426/648; 426/655

(58) Field of Search ............................... 424/725, 93.3, 424/736, 777, 778, 773, 774, 775, 776, 779; 426/531, 541, 542, 599, 615, 616, 623, 629, 630, 635, 648, 655

(56) References Cited

U.S. PATENT DOCUMENTS

| | | | | |
|---|---|---|---|---|
| 3,908,028 | A | * | 9/1975 | Neely et al. ................. 426/538 |
| 4,839,281 | A | | 6/1989 | Gorbach et al. |
| 5,032,399 | A | | 7/1991 | Gorbach et al. |
| 5,891,501 | A | | 4/1999 | McKellip et al. |
| 6,013,304 | A | * | 1/2000 | Todd ........................... 426/638 |

FOREIGN PATENT DOCUMENTS

| | | |
|---|---|---|
| GB | 1501098 | 2/1978 |
| JP | 56018565 | 2/1981 |
| WO | WO 95/16461 | 6/1995 |
| WO | WO 96/37210 | 11/1996 |
| WO | WO 99/08532 | 2/1999 |

OTHER PUBLICATIONS

Gruenwald, J. et al (eds.). PDR for Herbal Medicines. 1998. Medical Economics company, Montvale, N.J., pp. 646–647, 890, and 1022–1025.*

Type 1 pili–mediated adherence of *Escherichia coli* strain LF82 isolated from Crohn's disease is involved in bacterial invasion of intestinal epithelial cells, Boudeau, et al, Molecular Microbiology (2001) 39(5), pp. 1272–1284.

Regulation of Type 1 Pili Expression as Exemplified by *Escherichia Coli* Strain M17, Chesnokova, et al., Bulletin of Experimental Biology and Medicine, No. 4, 2001, Immunology and Microbiology, pp. 977–980.

Characterization of New Plasmids from Methylotrophic Bacteria, et al, Antonie van Leeuwenhoek 60: 1991, pp. 43–48.

Transcriptional Regulation of lux Genes Transferred into *Vibrio harveyi*, Miyamoto, et al., Journal of Bacteriology, Apr. 1990, vol. 172, No. 4, pp. 2046–2054.

Intergeneric Conjugal Transfer of *Escherichia coli*/Methylobacterium sp. Shuttle Vector, Holubova, et al., Folia Microbiol., 38(4) 1993, pp. 277–280.

Influence of Certain Inhibitors on the Viability of Protein and Nucleic Acid Synthesis in *Escherichia Coli*, Avtushenko et al., Microbiology, May–Jun. 1985, vol. 54, No. 3, pp. 319–322.

*Lactobacillus plantarum* 299v Inhibits *Escherichia coli*–induced Intestinal Permeability, Mangell, et al., Digestive Diseases and Sciences, vol. 47, No. 3, Mar. 2002, pp. 511–516.

Specific Proliferative and Antibody Responses of Premature Infants to Intestinal Colonization with Nonpathogenic Probiotic *E–coli* Strain Nisslw 1917, Cukrowska, et al., Immunol 55, 2002, pp. 204–209.

A New Biological Agent for Treatment of Shiga Toxigenic *Escherichia coli* Infections and Dysentery in Humans, Nature Medicine, vol. 6, No. 3, Mar. 2000, pp. 265–270.

Probiotic Fermented Food Mixeer: Possible Applictions in Clinical Anti–Diarroea Usage, Rani et al., Nutrition and Health, 1998, vol. 12, pp. 97–105.

Antagonistic Effect of *Lactobacillus Acidophilus, Saccharomyces Boulardii* and *Escherichia Coli* Combinationa Against Experimental Infections with *Shigella Flexneri* and *Salmonella Enteritidis* Subsp. Typhimurium in Gnotobiotic Mice, Filho–Lima, et al. Journal of Applied Microbiology 2000, 88, pp. 365–370.

(List continued on next page.)

Primary Examiner—Christopher R. Tate
Assistant Examiner—Kailash C. Srivastava
(74) Attorney, Agent, or Firm—G. E. Ehrlich Ltd.

(57) ABSTRACT

The present invention discloses: (i) a non-pathogenic probiotic microorganism and its probiotic/therapeutic uses; (ii) a formulation comprising an aqueous solution of a volatile fraction (VF) prepared from the extract of at least one plant derived material and its therapeutic uses; (iii) a process of manufacturing the formulation from the plant derived material; (iv) a probiotic composition comprising the non-pathogenic probiotic microorganism of the invention and/or other probiotic microorganism(s) and the formulation of the invention, and its probiotic/therapeutic uses; (v) a composition for industrial applications comprising the formulation of the invention and microorganism(s) of industrial applicability; and (vi) industrial processes and apparatuses in which the latter composition is used.

4 Claims, 1 Drawing Sheet

OTHER PUBLICATIONS

Symposium: Probiotic Bacteria: Implications for Human Health, Rolfe, American Society for Nutritional Sciences, 2000, pp. 396S–402S.

The Effect of Probiotic Bacteria on the Adhesion of Pathogens to Human Intestinal Mucus, Tuomola, et al., Federation of European Microbiological Societies Immunology and Medical Microbiology, 26, 1999, pp. 137–142.

Characterizatio of the Integration Site of Yersina High–Pathogenecity Island in *Escherichia Coli*, Schubert, et al., Federation of European Microbiology Societies Letters, 179, 1999, pp. 409–414.

Probitics and *E–Coli* Infections in Man, Lodinova–Zadnikova et al., National Library of Medicine, 1999, vol. 20, Issue 3, Supplement, 5 pages.

Reduction of Carriage of Enterohemorrhagic *Escherichia Coli* O157:H7 in Cattle by Inoculation with Probiotic Bacteria, Zhao, et al., Journal of Clinical Microbiology, Mar. 1998, vol. 36, No. 3, pp. 641–647.

The Possible Role of Probiotics as Dietary Antimutagens, Renner, et al., Mutation Research, 262, 1991, pp. 239–245.

Induction of the Phage Resistance in the Progeny of an Infected Bacterial Cell, Pererva, Biopolymers and Cell, vol. 15, N1, 1999, pp. 63–66.

Properties of Strains of *Escherichia Coli* Isolated from the Faeces of Patients with Ulcertative Colities, Patients with Acute Diarrhoea and Normal Persons, Cooke, Journal fo Pathology and Bacteriology, vol. 95, No. 1, Jan. 1968, pp. 101–113.

Ulcertative Colitis and *Escherichia Coli* with Adhesive Properties, Burke, et al., Journal Clinical Pathology, 1987, 4, pp. 782–786.

Virulence Properties of *Escherichia Coli* Strains Isolated from Patients with Inflammatory Bowel Diseases, Giaffer, et al., GUT, 1992, 33, pp. 646–650.

Probiotics: Towards Demonstrating Efficacy, Mattila–Sandholm et al., Trends in Food Sciences & Technology, 10, 1999, pp. 393–399.

Recolonization Therapy with Nonadhesive *Escherichia Coli* for Treatment of Inflammatory Bowel Disease, McCann, et al., Microbial Pathogenesis and Immune Response, vol. 730, 1994, pp. 243–245.

Oral Administration of a Certain Strain of Live *Escherichia Coli* for Intestinal Disorders? Beutin, Infection 23, 1995, No. 1, pp. 51/55–62/188.

Properties of *Escherichia Coli* Strains of Serotype O6, Blum et al., Infection, 23, 1995, No. 4, pp. 46/234–48/236.

Microbiologists on the Trail of Polluting Bacteria, Malakoff, Science, vol. 295, Mar. 29, 2002, pp. 2352–2353.

Invasive Ability of an *Escherichia coli* Strain Isolated from the Ileal Mucosa of a Patient with Crohn's Disease, Boudea, et al., Infection and Immunity, Sep. 1999, vol. 67, No. 9, pp. 4499–4509.

Pathologic and Physiologic Interactions of Bacteria with the Gastrointestinal Epithelium[1–3], Lei Lu, et al., Am. J. Clin. Nutr. 2001, 73, (supplement), pp. 11248–11308.

Novigen Document Order #5, 36 articles, May 2, 2002, pp. 1–11.

Characterization of New Plasmids from Methylotrophic Bacteria, Breener, et al., Antonie van Leeuwenhoek, 60: 1991, pp. 43–48.

Displacement of *Escherichia coli* O157:H7 from Rumen Medium Containing Prebiotic Sugars, de Vaux, et al., Applied and Environmental Microbiology, Feb. 2002, vol. 68, No. 2, pp. 519–524.

Inhibitory Activity of *Bifidobacterium Longum* HY8001 Against Vero Cytotoxin of *Escherichia coli* O157:H7, Kim et al., Journal of Food Protection, vol. 64, No. 11, 2001, pp. 1667–1673.

Effect of Probiotiex on Enteocyte Bacterial Translocation in vitro, Mattar et al., Pediatric Surgery Int., 2001, 17, pp. 265–268.

A Dietafry Probiotic (*Bifidobacterium Lactis* HN019) Reduces the Severity of *Escherichia coli* O157:H7 Infection in Mice, Shu, et al., Med. Microbiol Immunol, 2001, 189, pp. 147–152.

Probiotic Treatment Using *Bifidobacterium lactis* HN019 Reduces Weanling Diarrhea Associated with Rotavirus and *Escherichia coli* Infection in a Piglet Model, Shu, et al., Journal of Pediatric Gastroenterology and Nutrition, 33, pp. 171–177.

In vitro Adherence Properties of *Lactobacillus rhamnosus* DR20 and *Bifidobacterium lactis* DR10 Strains and their Antagonistic Activity Against an Enterotoxigenic *Escherichia coli*, Gopal, et al., International Journal of Food Microbiolgy, 67, 2001, pp. 207–216.

Antimicrobial Activity of Intraurethrally Administered Probiotic *Lactobacillus casei* in a Murine Model of *Escherichia coli* Urinary Tract Infection, Asahara, et al., Antimicrobioal Agents and Chemotherapy, Jun. 2001, vol. 45, No. 6, pp. 1751–1760.

Probiotic Activities of *Lactobacillus casei* rhamnosus: in vitro Adherence to Intestinal Cells and Antimicrobial Properties, Forestier, et al., Res. Microbiol. 152, 2001, pp. 167–173.

*Lactobacillus plantarum* Reduces Infection of Pancreatic Necrosis in Experimental Acute Pancreatitis, Mangiante, et al., Digestive Surgery, 2001, 18, pp. 47–50.

Significance of Fecal Volatile Fatty Acids in Shedding of *Escherichia coli* O157 from Calves: Experimental Infection and Preliminary Use of a Probiotic Product, Ohya, et al., J. Vet. Med. Sci. 62, 11, 2000, pp. 1151–1155.

A Strain of *Enterococcus faecium* (18C23) Inhibits Adhesion of Enterotoxigenic *Escherichia coli* K88 to Porcine Small Intestine Mucus, Jin et al., Applied and Environmental Microbiology, Oct. 2000, vol. 66, No. 10, pp. 4200–4204.

Evaluation of Probiotic Treatment in a Neonatal Animal Model, Lee et al., Pediatr. Surg. Int. 2000, 16, pp. 237–242.

Expression of *Clostridium thermocellus* Endoglucanase Gene in *Lactobacillus gasseri* and *Lactobacillus johnsonii* and Characterization of the Genetically Modified Probiotic Lactobacilli, Soon–Chuo, et al., Current Microbiology, vol. 40, 2000, pp. 257–263.

Probiotic Therapy with *E. coli* for Ulcerative Colitis: Take the Good with the Bad, Binder, et al., Gastroenterology 2000, 118, pp. 630–631.

Immunomodulatory Effects of *Lactobacillus plantarum* Colonizing the Intestine of Gnotobiotic Rats, Herias, et al., Clin. Exp. Immunol 1999, 116, pp. 283–290.

Probiotics Inhibit Enteropathogenic *E. coli* Adherence in vitro by Inducing Intestinal Mucin Gene Expression, Mack, et al., American Physiological Society, 1999, pp. G941–G950.

Monoassociation with *Lactobacillus acidophilus* UFV–H2b20 Stimulates the Immune Defense Mechanisms of Germfree Mice, Neumann, et al., Brazilian Journal of Medical and Biological Research 1998, 31, pp. 1565–1573.

Adhesion of Some Probiotic and Dairy Lactobacillus Strains to Caco–2 Cell Cultures, Tuomola, et al., International Journal of Food Microbiology, 41, 1998, pp. 45–51.

Effect of Fermented Milk Intake on Plasmid Transfer and on the Persistence of Transconjugants in the Digestive Tract of Gnotobiotic Mice, Duval–Iflah, et al., Antonie van Leeuwenhoek, 73, 1998, pp. 95–102.

Inhibition of in vitro Growth of Enteropathogens by new Lactobacillus Isolates of Human Intestinal Origin, Drago, et al., Federation of European Microbiological Societies Microbiology Letters, 153, 1997, pp. 455–463.

The Effect of *Lactobacillus Salivarius* Administration on Coliforms and Enterococci in the Crop and Caeca of Chicken Broilers, Rada, et al., Vet. Med. Czech, 40, 1995, 10, pp. 311–315.

Data on the Effects of the Probiotic "Lacto Sacc" Kovacs–Zomborszky, et al., Acta Veterinaria Hungarica 42, 1, 1994, pp. 3–14.

The Effect of Lactobacillus spp. on the Attachment of Enterotoxigenic *Escherichia coli* to Isolated Porcine Enterocytes, Spencer, et al., Journal of Applied Bacteriology, 1994, 77, pp. 215–220.

Distribution of Pathogen Inhibition in the Lactobacillus Isolates of a Commericial Probiotic Consortium, Chateau, et al., Journal of Applied Bacteriology, 1993, 74, pp. 36–40.

Evaluation of the Effect of 3 Probiotics on Experimental *Escherichia coli* Enterotoxaemia in Weaned Piglets, Cupers et al., J. Vet. Med. B. 39, 1992, pp. 277–284.

Regulation of the Gut Flora Via Food, Gedek, Zbl. Hyg., 191, 1991, pp. 277–301.

Streptococcu Faecium M74 in Control of Diarrhea Induced by a Human Enterotoxigenic *Escherichia coli* Strain in an Infant Rabbit Model, Wadstroem, Zbl., Bakt., Hyg., A 257, 1984, pp. 357–363.

Antibacterial Activity of Strains Used in the Dairy Industry, Warminska–Radyko et al., Med. Fac. Landbuoww. Univ. Gent. 65/3b, 2000, pp. 559–562.

Characterization of New Plasmids from Methylotrophic Bacteria, Brenner, et al., Antonie van Leeuwenhoek 60, 1991, 43–48.

Transcriptional Regulation of lux Genes Transferred in *Vibrio harveyi*, Miyamoto, et al., Journal of Bacteriology, Apr. 1990, vol. 172, No. 4, pp. 2046–2054.

Study on Small Intestinal Lumenal and Membrane Flora of 30 Healthy Chinese, Ling jia, et al., Chinese Journal of Internal Medicine, vol. 35, Oct. 1996, No. 10, pp. 686–689.

Nutritive Effects of Bacillus Cereus on the Rearing of Piglets, Gedek et al., Arch. Anim. Nutr., 1993, vol. 44, pp. 215–226.

* cited by examiner

BACTERIAL STRAIN, PROCESSES PLANT EXTRACTS, COMPOSITIONS CONTAINING SAME, PROCESSES FOR THEIR PREPARATION AND THEIR THERAPEUTIC AND INDUSTRIAL APPLICATIONS

This is a Divisional Application of U.S. application Ser. No. 09/725,846 filed Nov. 30, 2000, which is pending, which is a Continuation-in-Part of PCT application Ser. No. IL00/00318, filed Jun. 1, 2000.

FIELD AND BACKGROUND OF THE INVENTION

The present invention relates to (i) a non-pathogenic probiotic microorganism and its probiotic/therapeutic uses; (ii) a formulation comprising an aqueous solution of a volatile fraction (VF) prepared from the extract of at least one plant derived material and its therapeutic uses; (iii) a process of manufacturing the formulation from the plant derived material; (iv) a probiotic composition comprising the non-pathogenic probiotic microorganism of the invention and/or other probiotic microorganism(s) and the formulation of the invention, and its probiotic/therapeutic uses; (v) a composition for industrial applications comprising the formulation of the invention and microorganism(s) of industrial applicability; and (vi) industrial processes and apparatuses in which the latter composition is used.

Under normal conditions, the gastrointestinal (GI) tract microflora contributes significantly to the health and well being of an individual. It is well known that the microflora is a complex and diverse population of microorganisms, which may have both beneficial and harmful effects on the individual. Under normal gestation conditions, the fetus in utero is sterile, but on passage through the vagina during birth it acquires microorganisms resulting in the formation of a gut microflora. The final indigenous gut microflora which stabilizes in the gut is a very complex collection of over one thousand different types of microorganisms, consisting of about 400 different types of bacteria [Fuller R. J. Applied Bacteriology 66:365–378 (1989)]. The composition of the gut microflora is determined by both host and microbial factors, and although there are a lot of bacteria which can survive and grow in the GI tract, there are many which cannot. In addition, the surviving organisms have to avoid the effect of peristalsis which normally flushes out the bacteria with the food. This may be achieved by the bacteria immobilizing themselves by attachment to the gut wall, and/or by multiplying at a rate that exceeds the rate of removal by peristalsis.

In general, the presence of gut microflora is symbiotic as the microflora not only assists in disintegrating some undigestable foods, it also protects the individual from infections caused by pathogens. This latter phenomenon has been described under such names as 'bacterial antagonism', 'bacterial interference', 'barrier effect', 'colonization resistance', 'competitive exclusion' and many others.

The gut protective microflora is very stable. However, it is less effective in the young, elderly and the compromised patient. Further, it can be influenced by certain dietary and environmental factors, the three most important being excessive hygiene, antibiotic therapy and stress.

Under conditions where the balance of the gut microflora is adversely affected, probiotics become of potential value in restoring the gut microflora and enabling the individual host to return to normal.

Probiotics are a class of microorganisms defined as live microbial organisms that beneficially affect the animal and human hosts. The beneficial effects include improvement of the microbial balance of the intestinal microflora or improving the properties of the indigenous microflora. The beneficial effects of probiotics may be mediated by a direct antagonistic effect against specific groups of organisms, resulting in a decrease in numbers, by an effect on their metabolism or by stimulation of immunity. Probiotics may suppress viable counts of an undesired organism by producing antibacterial compounds, by competing for nutrients or for adhesion sites. Further, they may alter microbial metabolism by increasing or decreasing enzyme activity or they may stimulate the immune system by increasing antibody levels or increasing macrophage activity.

WO95/16461 describes a probiotic composition of anaerobic bacteria effective in controlling or inhibiting Salmonella colonization in domesticated animals. The probiotic composition includes populations or cultures of 29 substantially biologically pure bacteria, inter alia, *E. coli*. However, the suppression of the pathogen by the probiotic composition described in this PCT publication requires the combined action of a large number of bacterial strains.

WO97/35596 describes the administration of a freshly prepared probiotic mixture obtained by mixing a powder containing *Lactobacillus reuteri*, *Lactobacillus acidophilus* and *Bifidobacterium infantis* with a liquid. The mixture is described to be effective in preventing infectious diarrhea or diarrhea caused by antibiotic therapy in humans. The freeze-dried live bacteria are, however, in anabiotic state. The need to wet the microorganism before administration, in order to reinstate its vitality, is a disadvantage, since normally many bacteria do not survive the re-hydration. Moreover, the surviving organisms are not immediately metabolically active, and cannot survive the extreme, acidic conditions of the stomach. Furthermore, when administered to a recipient with diarrhea, the rate of their removal from the gut may exceed the rate of reinstation of viability, resulting in minimal or no beneficiary effect.

Preservation of viability and conservation of the activity of probiotic organisms by their formulation is the issue of numerous publications. WO98/26787 describes the enhancement of a resident population of lactic acid-producing microorganisms, preferably *lactobaccillii*, in the GI tract of an animal by providing the same with β-glucan, optionally in combination with prebiotic and/or probiotic microorganisms.

WO97/34591 also describes the enhancement of resident population of microorganisms, or the suppression of the undesired resident population at a selected site of the GI tract of an individual, by providing the individual with a selected modified or unmodified starch or mixtures thereof, which act as carrier for one or more probiotic microorganisms and as a growth or maintenance medium for the microorganisms. The probiotic elements are bound to the carrier in a manner so as to protect the microorganisms during passage to the large bowel or other regions of the GI tract.

Microorganisms are used in a variety of industrial processes. These processes can be divided into continuous processes and batch processes. In continuous processes, such as a continuous aerobic or anaerobic fermentation line, used for the production of a variety of fermentation products, including, for example, ethanol and methanol, a fermentable raw material is continuously fed into the line and the fermentive product is continuously collected from the line, in a controlled fashion, such that the microorganism population in the line is sustained throughout the process. In batch processes, such as, but not limited to, batch aerobic or anaerobic fermentation, biodegradation of oil in, for example, oil spills, and the like, a fermentable raw material is mixed with a population of microorganism(s) so as to instate fermentation. Both in continuous fermentation and in batch fermentation processes, it is desired, in some cases, to start or reinstate the process with a large and viable population of the relevant microorganism(s). For example, when biodegrading oil, it is advantageous to start the process with an as large as possible population of the microorganisms Pseudomonas spp. or Alcaligenes spp., for example, so as to minimize the time for complete biodegradation of the oil. When using filters enriched with microorganism(s) for biodegradation of organic fumes or volatiles, the result is a continuous process in which polluting compounds are degraded into harmless compounds. However, the microorganisms present in the filter depend for their survival on continuous supply of organic fumes or volatiles. Nevertheless, in some instances the supply of organic fumes or volatiles is discontinued and, as a result, the microorganism(s) are lost. Under such circumstances, reinstation of an effective viable amount of microorganism(s) in the filter is required in a short period of time, so as permit immediate restoration of a functional filter.

There is thus a widely recognized need for, and it would be highly advantageous to have, a formulation in which microorganisms, including probiotic microorganisms and microorganisms useful in a variety of industrial applications, could be maintained viable and in a metabolically active form for long periods of time.

While reducing the present invention to practice, it has been unexpectedly found that a single species of a non-pathogenic probiotic microorganism derived from *E. coli* is, alone, capable of restoring normal GI flora of man and of a variety of mammals and avians. It has also been surprisingly found that this microorganism, as well as other microorganisms, could be preserved for long periods of time, in a viable and metabolically active form, in a formulation comprising water solution of volatile fraction(s) of various plant extracts. A probiotic composition comprising the probiotic organism suspended in the formulation was found to be effective in the treatment and prevention of various gastrointestinal disorders. It has further been unexpectedly found that the formulation per se is effective as a body weight gain enhancer and as an immuno-stimulator in mammals and avians.

SUMMARY OF THE INVENTION

According to one aspect of the present invention there is provided an *Escherichia coli* strain BU-230–98 ATCC Deposit No.20226 (DSM 12799).

According to another aspect of the present invention there is provided a probiotic composition comprising viable *Escherichia coli* strain BU-230–98 ATCC Deposit No. 20226 (DSM 12799) and a formulation for maintaining viability of the *Escherichia coli* strain. The probiotic composition preferably further comprising at least one flavouring agent. Preferably, the formulation includes at least one volatile fraction (VF) of a plant extract prepared by steam distillation of a plant (e.g., beet, dill, parsley or grapefruit) extract under reduced pressure and at a bath temperature preferably not exceeding 38° C.

The probiotic composition of the present invention may be identified for preventing or treating gastro-enteric infections or disorders, maintaining or reinstating normal gastrointestinal microflora, preventing or treating diarrhea, preventing or treating gastro-enteric infection caused by an enteric pathogen, such as a Gram negative bacterium or Gram positive bacterium, preventing or treating gastroenteric Salmonella infection, preventing or treating infectious diarrhea, caused by, for example *C. difficile*, Salmonella, particularly *S. Shigella*, Campylobacter, *E. coli*, Proteus, Pseudomonas or Clostridium, chronic diarrhea or diarrhea resulting from antibiotic therapy, radiotherapy or chemotherapy, and/or for normalizing the physiological activity of the gastrointestinal tract.

According to yet another aspect of the present invention there is provided a formulation comprising at least one volatile fraction (VF) of a plant extract, the volatile fraction is prepared by steam distillation of the plant extract under reduced pressure and at a bath temperature not exceeding 38° C. The plant extract is preferably obtainable from a plant organ selected from the group consisting of leaves, stems, roots and fruit. The plant can be a vegetable, such as soy bean, alfalfa, garlic, beet and cabbage, or a herb, such as parsley, mint and dill. The formulation may further include a beehive product, such as, but not limited to, propolis. The formulation can serve as a veterinary feed or food additive for enhancing animal weight gain in a recipient. It can also serve to preserve viable bacteria as is further described herein.

Hence, according to an additional aspect of the present invention there is provided a process of preparing a volatile fraction of a plant, comprising the steps of (a) grinding a plant derived material to give a plant biomass; (b) mixing the plant biomass with water and stirring at ambient temperature; (c) steam distilling the mixture obtained in step (b) under reduced pressure and at a bath temperature not exceeding 38° C.; and (d) collecting volatile fraction obtained from the steam distillation. Preferably, the reduced pressure is of 5–10 mbar. This formulation can be used as a food additive, a feed additive and has unexpected therapeutic uses, as well as advantageous bacteria preservation properties. A therapeutic formulation containing the volatile fraction of a plant is also disclosed and may be prepared by mixing at least one volatile fraction (VF) of a plant extract with physiologically or veterinary acceptable additives, carriers or diluents. Preferably, the volatile fraction is prepared by steam distillation of the plant extract under reduced pressure and at a bath temperature not exceeding 38° C.

Thus, according to still another aspect of the present invention there is provided a probiotic composition comprising (a) an effective amount of at least one viable probiotic microorganism having a beneficial biological or therapeutic activity in the gastrointestinal tract; and (b) at least one volatile fraction (VF) of a plant extract preferably prepared as described herein. The probiotic microorganism can be *E. coli*, preferably, strain BU-230–98, ATCC Deposit No. 202226 and it can be identified for treatment or prevention of any of the above disorders/pathologies/diseases/syndromes and in addition or as an alternative in can be identified for treatment or prevention of dyspeptic symptoms, for enhancing the immune response in a patient suffering from an immune disorder, resulting from, for example, immune-response suppression therapy.

According to still another aspect of the present invention there is provided a composition comprising (a) at least one microorganism, such as, Escherichia spp., Alcaligenes spp., Arthrobacter spp., Bifidobacterium spp., Lactobacillus spp., Lactococcus spp., Nitrosomonas spp. and Pseudomonas spp.; and (b) at least one volatile fraction (VF) of a plant extract, the at least one volatile fraction is selected so as to sustain viability of the at least one microorganism for at least 2 months, preferably at least 3–6 months, more preferably 6–12 months or more at room temperature.

According to another aspect of the present invention there is provided a process of growing *Escherichia coli* strain BU-230–98 ATCC Deposit No. 20226 (DSM 12799), the process comprising the step of seeding a starter cloture of *Escherichia coli* strain BU-230–98 ATCC Deposit No. 20226 (DSM 12799) into a growth media and growing the *Escherichia coli* strain up to optical density of 15–30 at 650 nm.

According to yet another aspect of the present invention there is provided a process of manufacturing a probiotic composition, the process comprising the step of suspending viable *Escherichia coli* strain BU-230–98 ATCC Deposit No. 20226 (DSM 12799) in a formulation for maintaining viability of the *Escherichia coli* strain. Preferably, the formulation includes at least one volatile fraction (VF) of a plant extract, prepared, preferably by steam distillation of the plant extract under reduced pressure and at a bath temperature not exceeding 38° C., obtained from, for example, a plant organ selected from the group consisting of leaves, stems, roots and fruit, either a vegetable and a herb, such as soy bean, parsley, mint, dill, alfalfa, garlic, beet or cabbage.

According to still another aspect of the present invention there is provided a process of preparing a probiotic composition, the process comprising the step of suspending an effective amount of at least one viable probiotic microorganism having a beneficial biological or therapeutic activity in the gastrointestinal tract in an formulation containing at least one volatile fraction (VF) of a plant extract.

According to an additional aspect of the present invention there is provided a process of preparing a composition including viable microorganisms, the process comprising the step of suspending at least one microorganism in a formulation containing at least one volatile fraction (VF) of a plant extract, the at least one volatile fraction is selected so as to sustain viability of the at least one microorganism for at least 2 months at room temperature. The microorganism can be, for example, Escherichia spp., Ailcaligenes spp., Arthrobacter spp., Bifidobacterium spp., Lactobacillus spp., Lactococcus spp., Nitrosomonas spp. or Pseudomonas spp.

According to yet an additional aspect of the present invention there is provided a dispenser of microorganisms comprising a reservoir and a dispensing mechanism being connected thereto, the reservoir housing at least one microorganism in a formulation containing at least one volatile fraction (VF) of a plant extract, the at least one volatile fraction is selected so as to sustain viability of the at least one microorganism for at least 2 months at room temperature.

According to still an additional aspect of the present invention there is provided a method of biocontrol of an organism, the method comprising the step of spreading in an endemic area at least one viable microorganism capable of biocontrolling the organism, the at least one viable microorganism being in a formulation containing at least one volatile fraction (VF) of a plant extract, the at least one volatile fraction is selected so as to sustain viability of the at least one microorganism for at least 2 months at room temperature.

According to a further aspect of the present invention there is provided a method of eliminating an oil pollution, the method comprising the step of spreading in a polluted area at least one viable microorganism capable of degrading oil, the at least one viable microorganism being in a formulation containing at least one volatile fraction (VF) of a plant extract, the at least one volatile fraction is selected so as to sustain viability of the at least one microorganism for at least 2 months at room temperature.

According to yet a further aspect of the present invention there is provided a method of restoring organic fumes degrading microorganism population in a biofilter, the method comprising the step of dispensing onto the filter at least one viable microorganism capable of degrading organic fumes, the at least one viable microorganism being in a formulation containing at least one volatile fraction (VF) of a plant extract, the at least one volatile fraction is selected so as to sustain viability of the at least one microorganism for at least 2 months at room temperature.

According to still a further aspect of the present invention there is provided a method of preparing a starter for a fermentation process, the method comprising the step of growing a sufficient amount of a starter microorganism and suspending the starter microorganism in a formulation containing at least one volatile fraction (VF) of a plant extract, the at least one volatile fraction is selected so as to sustain viability of the starter microorganism for at least 2 months at room temperature.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF THE INVENTION

Figure 1:
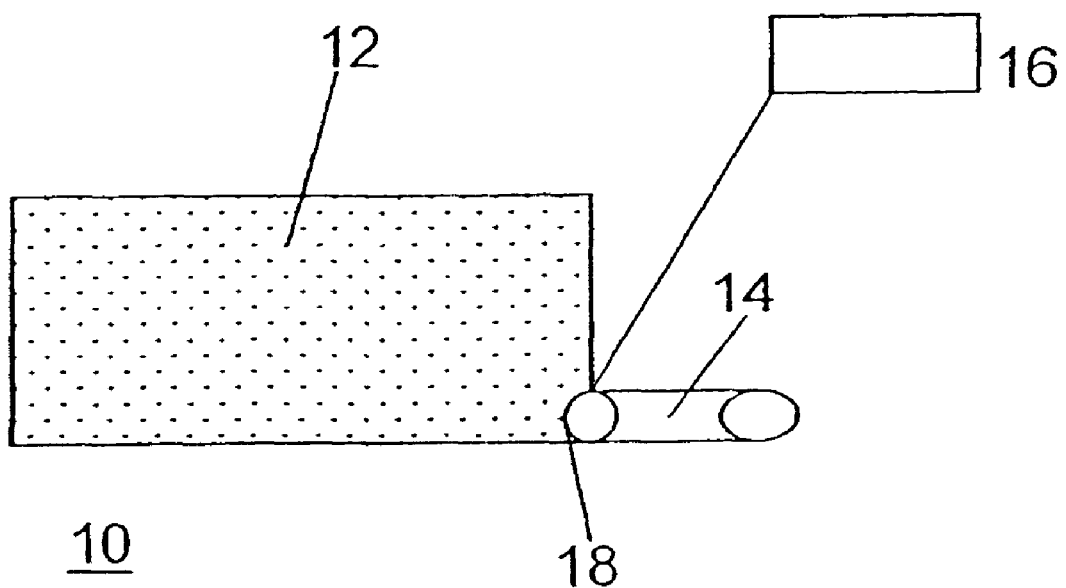
FIG. 1 is a schematic depiction of a dispenser according to the present invention.

The present invention is of (i) a non-pathogenic probiotic microorganism and its probiotic/therapeutic uses; (ii) a formulation comprising an aqueous solution of a volatile fraction (VF) prepared from the extract of at least one plant derived material and its therapeutic uses; (iii) a process of manufacturing the formulation from the plant derived material; (iv) a probiotic composition comprising the non-pathogenic probiotic microorganism of the invention and/or other probiotic microorganism(s) and the formulation of the invention, and its probiotic/therapeutic uses; (v) a composition for industrial applications comprising the formulation of the invention and microorganism(s) of industrial applicability; and (vi) industrial processes and apparatuses in which the latter composition is used.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

In one aspect, the present invention relates to a probiotic microorganism being a non-pathogenic bacterium derived from *E. coli,* having a beneficial physiological and/or therapeutic activity in, for example, the GI tract and deposited at the ATCC under deposit No. 202226 and at DSMZ under deposit No. 12799.

"Probiotic" is used herein as an adjective to describe an isolated bacteria having the property of inhibiting the growth of at least one pathogen. The test of an inhibition used herein was an in vitro test on solid medium in which culture supernatants of candidate isolated bacteria were observed for their property of inhibiting the growth of a pathogen when applied to the surface of the solid medium. Typically, a paper disc impregnated with the culture supernatant of a candidate probiotic strain was placed on the surface of an agar plate seeded with the pathogen. Probiotic bacterial supernatants caused a ring of clear agar or of reduced growth density indicating inhibition of the pathogen in the vicinity of the disc. There are other tests for inhibition which are available or could be devised, including direct growth competition tests, in vitro or in vivo which can generate a panel of probiotic bacteria similar to that described herein. The bacterial strains identified by any such test are within the category of probiotic bacteria, as the term is used herein.

The probiotic bacteria of the present invention may serve as a food or feed additive, so as to provide food or feed product supplemented with viable *Escherichia coli* strain BU-230–98 ATCC Deposit No. 20226 (DSM 12799). A food product of the present invention may further include at least one milk derived substance and may be selected from the group consisting of a cheese and a yogurt.

The present invention further relates to a formulation comprising at least one volatile fraction (VF) of a plant extract, the volatile fraction being prepared by distillation of the plant extract under reduced pressure and at a bath temperature typically not exceeding 38° C.

The plant matter from which the volatile fraction may be obtained may be any suitable plant part such as fruit, leaf, stem or root. Many plants are suitable as a source for the volatile fractions, for example apple, citrus, soy bean, beet, cabbage, garlic and alfalfa, as well as herbs such as parsley, mint and dill. The formulations of the invention may optionally further comprise a suitable amount of a volatile fraction of an apicultural product such as honey, propolis or other beehive product, which may be prepared in the same manner as described herein for obtaining volatile fractions from plant extracts.

As will be described in more detail in the following Examples, the formulation itself may be used as a food/feed additive. It has been found by the inventors to have a weight gain enhancing activity and it constitutes an aspect of the invention. According to a particular embodiment of this aspect of the invention, the animal weight gain enhancing formulation or feed additive comprises distilled water and volatile fractions of alfalfa, soy beans, beet and dill, preferably at a volume ratio of the volatile fractions of 2:8:1:4. Alternatively, a formulation or feed additive of the present invention comprises distilled water and volatile fractions of carrot, beet, dill and grapefruit (1 part each) per 100 parts of water. Still alternatively, a formulation or food additive of the present invention comprises distilled water and volatile fractions of beet, dill and parsley (1 part each) per 100 parts of water.

In a further aspect, the invention relates to a composition comprising the above formulation of the invention and at least one viable microorganism, either a probiotic organism having a therapeutic or beneficial biological activity in, for example, the GI tract of human and/or animal, to thereby provide a probiotic composition, or an organism having industrial applications, to thereby provide a composition of industrial applicability.

A particular advantage of the probiotic and industrial compositions of the invention stems from the fact that they are liquid preparations. Being under biologically active conditions, the formulation serves also as a supportive medium for living bacteria, as opposed to lyophilized formulations where the bacteria are in an anabiotic condition. As a result, the probiotic composition of the invention, for example, is active immediately following oral administration, beginning with the upper portion of the GI tract, where primary effects of the majority of intestinal pathogens take place, causing development of adverse gastro-enteric syndromes. The probiotic compositions of the invention may also be used as body weight-increasing preparations or food/feed additives. Similarly, the industrial composition of the invention can be used to efficiently reinstate a population of microorganisms of industrial applicability.

Thus, it is noted that, for probiotic applications, probiotic bacteria other than such belonging to the strain BU-230–98 (ATCC Deposit No. 202226, also deposited at the DSM under No. 12799), may be used with the plant material derived formulation of the invention. Such probiotic bacteria have a very broad spectrum of antagonistic activity. They also belong to the same phylogenetic group of the majority of intestinal pathogens and share the same systems of survival. Therefore, the suppression and exclusion of intestinal pathogens may include many different mechanisms, for example, secretion of antagonistic material, competition for utilization of nutrients and competition for adhesion receptors. Thus, any non-pathogenic bacteria which comply with these criteria, may be used in the probiotic compositions of the invention.

According to a further aspect of the invention, the probiotic compositions of the invention may be used for preventing or treating gastro-enteric infections. Term 'gastroenteric infection' is to be taken to mean any infection caused an enteric pathogen, including, inter alia, Gram negative and Gram positive bacteria. By improving the general balance and health of the GI tract, the formulations and probiotic compositions of the invention may be instrumental in prophylaxis of also GI infections caused by yeast, viruses and protozoa.

The term 'therapeutically effective amount' or 'effective amount' for purposes herein is the amount determined by such considerations as are known in the art. The amount must be sufficient to enable the efficient restoration of the GI microflora thus leading to the normalization of the function of the GI tract.

In a particular embodiment, the probiotic composition for preventing the development of gastro-enteric infections comprises the formulation of the invention made from distilled water and volatile fractions of alfalfa, soy beans, beet, dill and mint as defined herein, at a volume ratio of, e.g., 5:1:5:15: 1, and a therapeutically effective amount of a probiotic bacteria such as *E. coli* ATCC Deposit No. 202226 (identical with DSM 12799) or any other probiotic bacteria.

A specific example for an gastro-enteric infection is that caused by Salmonella and the invention is of particular advantage in preventing or treating gastro-enteric infections caused thereby.

Further, the food additive or formulation of the invention, alone or in combination with an effective amount of a probiotic microorganism, such as the *E. coli* strain ATCC Deposit No. 202226 (identical with DSM 12799), may be used for treating or preventing infectious diarrhea, chronic diarrhea or diarrhea caused by antibiotic or chemotherapy.

According to a further specific embodiment of the invention, such a probiotic composition for treating diarrhea may comprise distilled water and volatile fractions of alfalfa, soy beans, beet, dill and mint at a volume ratio of, e.g., 5:1:5:15:1, and a therapeutically effective amount of the ATCC No. 202226 (DSMZ 12799).

The infectious diarrhea may be caused by numerous factors, for example, by a microorganism selected from *C difficile*, Salmonella, particularly S. Shigella, Campylobacter, *E. coli*, Proteus, Pseudomonas, Clostridium, enteric Staphylococcus. These are but few of many infecting agents.

Yet further, the probiotic compositions of the invention may be used for effectively restoring the GI microflora in a subject in need of such treatment which leads to the normalization of the function of the GI tract. Such compositions may include, for example, distilled water and volatile fractions of alfalfa, soy bean, beet, dill, mint, parsley and cabbage, preferably at a ratio of volatile fractions of, e.g., 1:5:5:2:2:1, and a therapeutically effective amount of the probiotic bacteria ATCC Deposit No. 202226 (DSM 12799).

Other purposes for which the probiotic compositions of the invention, comprising at least one probiotic bacteria having a therapeutic effect in, for example, the GI tract, include alleviation of lactose intolerance in subjects suffering from lactose intolerance, treatment of enterocolitis, treatment of constipation, for reduction of cholesterol levels in the blood, for treatment of dyspeptic symptoms, and/or for stimulation of the immune system in subjects suffering from an immune system disorder, which may be an immune disorder caused by immuno-suppressive therapy.

In a different aspect, the invention relates to a process for preparing a volatile fraction of a plant extract, which process comprises the steps of: (a) grinding plant derived matter to obtain a plant biomass; (b) mixing the plant biomass obtained in step (a) with water at a weight proportion of preferably 3 parts water to 1 part of the plant biomass and stirring the same for at least 2 hours at ambient temperature; (c) distilling the mixture obtained in step (b) under reduced pressure and at a bath temperature preferably not exceeding 38° C.; and (d) collecting the volatile fraction obtained from the steam distillation, which fraction may further be diluted in a suitable buffer.

The volatile fraction of the invention may be mixed with water to give the food/feed additive or formulation of the invention. The food/feed additive or formulation of the invention may also be prepared by mixing more than one plant volatile fraction obtained by the process of the invention. This mixture may be further mixed with water.

The volatile fractions may be prepared from may any suitable fruit, vegetable, leaf, stem or root of a plant. The plant can be, for example, apple, citrus fruit, soy bean, beet, garlic, cabbage or alfalfa, or a herb such as parsley, mint or dill. It should be noted that when appropriate, the formulation may further comprise volatile fractions from apicultural products such as honey or propolis or other beehive products. These volatile fractions may be prepared in the same manner of the plant extract volatile fractions.

According to the process of the invention, the distillation step is preferably carried out under reduced pressure of 5–10 mbar.

As indicated hereinbefore, the food/feed additive or formulation of the invention may be further combined with at least one probiotic or industrial agent, to give the probiotic or industrial compositions of the invention. Thus, the process of preparation of the invention may also further comprise the step of suspending at least one viable probiotic or industrial microorganism in the volatile fraction obtained in said step (d) or in a mixture of such volatile fractions obtained as described above.

According to a particular process of the invention, the probiotic microorganism suspended may be the novel bacterium of the invention, derived from *E. coli* and deposited at the ATCC under Deposit No. 202226 (and at DSM under deposit No. 12799).

Finally, the invention relates to the use of a volatile fraction (VF) of a plant extract in the preparation of a food/feed additive, wherein the VF is prepared by steam distillation of said plant extract or from apiculture product extract such as honey or propolis at a bath temperature not exceeding 38° C.

An additional aspects of the invention include a process of preparing a composition including viable microorganisms. The process is effected by suspending at least one microorganism in a formulation containing at least one volatile fraction (VF) of a plant extract. The formulation is selected so as to sustain viability of the microorganism(s) for at least 2 months at room temperature. The microorganism of choice may be probiotic or have industrial applicability. Organisms which can be maintained in a formulation of the present invention include Escherichia spp., Alcaligenes spp., Arthrobacter spp., Bifidobacterium spp., Lactobacillus spp., Lactococcus spp., Nitrosomonas spp. and Pseudomonas spp.

As shown in FIG. 1, in another aspect the present invention provides a dispenser 10 of microorganisms. Dispenser 10 includes a reservoir 12 and a dispensing mechanism 14 connected thereto. Reservoir 12 houses at least one microorganism in a formulation containing at least one volatile fraction (VF) of a plant extract. The formulation is selected so as to sustain viability of the microorganism(s) for at least 2 months at room temperature. Reservoir 12 may be refrigerated, say to about 2–20° C., preferably to about 4° C. Dispenser 10 may be an airborne dispenser, so as to allow dispersion of pest control bioagents. The dispenser may be hand held. In any case, the dispenser may be designed to automatically dispense a predefined volume therefrom, e.g., periodically. To this end, dispenser 10 may include a programmable or preset control mechanism 16, valves 18, etc.

Thus, according to another aspect, the present invention provides a method of biocontrol of an organism which is effected by spreading in an endemic area at least one viable microorganism capable of biocontrolling the organism. The viable microorganism(s) are present in a formulation containing at least one volatile fraction (VF) of a plant extract selected so as to sustain viability of said at least one microorganism(s) for at least 2 months at room temperature.

Still according to another aspect the present invention provides a method of eliminating an oil pollution which is effected by spreading in a polluted area at least one viable microorganism capable of degrading oil, such as Pseudomonas spp. The viable microorganism(s) is present in a formulation containing at least one volatile fraction (VF) of a plant extract selected so as to sustain viability of said at least one microorganism for at least 2 months at room temperature.

Yet according to another aspect the present invention provides a method of restoring organic fumes degrading microorganism population in a biofilter by dispensing onto the filter at least one viable microorganism, such as Pseudomonas spp., Nitrosomonas spp., or Arthrobacter spp. capable of degrading organic fumes. The viable microorganism(s) is present in a formulation containing at least one volatile fraction (VF) of a plant extract selected so as to sustain viability of said at least one microorganism for at least 2 months at room temperature.

Still according to another aspect of the present invention there is provided a method of preparing a starter for a fermentation process by growing a sufficient amount of a starter microorganism, such as, Lactococcus spp., Escherichia spp., Bifidobacterium spp., Lactobacillus, Lactococcus spp. or Pseudomonas spp. and suspending the starter microorganism in a formulation containing at least one volatile fraction (VF) of a plant extract selected so as to sustain viability of said starter microorganism for at least 2 months at room temperature.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Preparation of a "volatile fraction" of plant extracts or extracts from apiculture products Fresh vegetables obtained from commercial markets were thoroughly washed by tap water, chopped and finely ground in an industrial blender. Distilled water was added to the vegetable biomass at the proportion of 3 parts water to 1 part of the vegetable mass by weight and left under stirring for at least 2 hours at ambient temperature.

The mixture was then transferred into the evaporating flask of a rotatory evaporator and was evaporated at a reduced pressure (5–10 mbar) under such conditions that the temperature of the water bath did not exceed 38° C., and that of the condenser inlet was 2–5° C. About 1 liter of the 2.5 kg of plant biomass.

This material could be preserved under refrigeration for at least 12 months without loosing its properties, as is further exemplified hereinunder.

The same procedure may be carried out, replacing the plant material with apiculture products such as honey or propolis.

Usually, each "volatile fraction" was prepared from a single kind of vegetable and used in different dilution to prepare different mixtures for various purposes.

Example 2

Isolation and growth of the probiotic organism E. coli ATCC Deposit No. 202226

The probiotic organism E. coli (deposited at the ATCC under No. 202226 on May 3, 1999 and at the DSM under No. 12799 on May 4, 1999) was isolated from E. coli M-17 by sequential transfer of isolates initiating from long term (2 months) survivors preserved in a formulation containing volatile fractions of plant derived material as is described under Example 1 above at 37° C. and selecting for isolates capable of competition with pathogens as is further detailed below. The probiotic organism E. coli (deposited at the ATCC under No.202226 on May 3, 1999 and at the DSM under No. 12799 on May 4, 1999) was grown in the following medium: $(NH_4)_2SO_4$-5 g/liter, $KH_2PO_4$-13 g/liter, $Na_2HPO_4$-13 g/liter, $MgCl_2$-3 g/liter, $CaCl_2$-0.3 g/liter, yeast extract—10 g/liter, Soy peptone—10 g/liter and glucose—5 g/liter. Additional nutrients (yeast extract—1 g/liter, Soy peptone—2.5 g/liter and glucose—90 g/liter) were continuously added following the growth of the culture in such a way that the glucose concentration in the fermentation broth was kept at a level of 2 g/liter. The pH of the fermentation broth was kept neutral by the continuous addition of 4N $NH_4OH$. Culturing was carried out at 30° C. in a standard fermentation vessel with aeration of 0.5 vvm for 16 hours, when the growth became confluent. This procedure resulted in $10^{10}$-$10^{11}$ cells/ml. The E. coli cells were harvested by centrifugation, resuspended in saline and re-precipitated. The microbial biomass could be kept in saline in the refrigerator for 48 hours without loosing viability.

Example 3

Preparation of food/feed additive formulation for the accelerated increase of body weight in mammals and avians The mixture contained volatile fractions of: alfalfa—50 ml/liter, soy beans—200 ml/liter, beet—25 ml/liter and dill—100 ml/liter, prepared as described under Example 1 above. The balance was made up by the distilled water.

Example 4

Preparation of a food supplement for the normalization of the function of the human GI tract The mixture contained volatile fractions of: alfalfa—50 ml/liter, soy beans—10 ml/liter, beet—50 ml/liter, dill—50 ml/liter, mint—20 ml/liter, parsley—20 ml/liter and cabbage—10 ml/liter, prepared as described under Example 1 above. The balance was made up by distilled water. E. coli (ATCC 202226) cells (Example 2) were suspended in the mixture at a cell concentration of $10^7$ cells/ml. NaCl (e.g., 4–10 g/liter) may be optionally added for the improvement of taste.

Example 5

Preparation of a feed additive formulation for the prophylaxis of GI infections in mammals and avians The mixture contained volatile fractions of: alfalfa—50 - ml/liter, soy beans—10 ml/liter, beet—50 ml/liter, dill—150 ml/liter and mint—10 ml/liter, prepared as described under Example 1 above. The balance was made by distilled water. E. coli (ATCC 202226) cells (Example 2) were suspended in the mixture at a cell concentration of $10^7$ cells/ml. NaCl (4–10 g/liter) may be optionally added for the improvement of the taste.

Example 6

**Antagonistic activity of *E. coli* (ATCC 202226) against *Salmonella typhymirium* (ATCC 14028)**

Petri plates containing Modified Brilliant Green Agar, a selective growth medium for Salmonella, were inoculated with *S. typhimirium*. A 9 mm diameter well was made in the agar. A volume of the food supplement (Example 4) was deposited in each well, and the plates were incubated for 24 hours at 35° C. The same was repeated, but instead of the food supplement, the fluid obtained by its filtration through a microbiological filter membrane (pore size of 0.45 µm) was deposited in the well.

Around each well containing the feed additive an inhibition zone (10–17 mm) devoid of *S. typhimirium* colonies was observed. No inhibition zone was observed around the wells containing the filtrate free of the probiotic organism.

Example 7

**Antagonistic activity of *E. coli* ATCC202226 as well as of its parent strain *E. coli* M-17 against Shigella sps.**

Cultures of *S. flexneri*, *S. sonnei*, *E. coli* (ATCC 202226) and M-17 were grown separately on a Nutrient Agar for 18–20 hours at 37° C. All the cultures were harvested in saline and diluted to an optical density of 10 Klett units. Aliquots of the diluted cultures of Shigella species (1 ml) alone or in combination with the diluted culture of *E. coli* (ATCC 202226) (1 ml) were seeded in ventilation-cup test tubes containing Nutrient Broth (5 ml). The tubes were incubated for 24 hours at 37° C. The number of colony-forming units (CFU) of the pathogens and of *E. coil* (ATCC 202226) was determined by plating the cultures on Nutrient agar. The CFU numbers of two Shigella species in the pure culture and in mixed cultures with both probiotic *E. coli* species are shown in Table 1 below.

TABLE 1

| | Growth of Shigella CFU/ml | |
|---|---|---|
| Probiotic Organism | *S. flexneri* | *S. sonnel* |
| *E. coli* ATCC 202226 | $<5 \times 10^4$ | $<5 \times 10^4$ |
| *E. coli* M-17 | $1 \times 10^6$ | $2 \times 10^6$ |
| Pure Shigella culture | $6 \times 10^6$ | $2 \times 10^6$ |

Example 8

**Application of the food supplement (Example 4) and of Colibacterin (dry formulation of *E. coli* M-17) in hospitalized gastroenteritis patients**

A group of 60 patients that developed gastroenteritis following hospitalization was randomly divided into 3 subgroups with a similar distribution of sex, age and the severeness of gasroenteritis symptoms. All patients received normal supportive treatment, including rehydration, vitamins, etc. The severity of condition did not require treatment with antibiotics. The first group of 20 patients received 10 ml of the food supplement (Example 5) 3 times daily 30 minutes before the meals for 7 days. The second group of the same number received Colibacterin (Colibacterinum siccum) as recommended by the producer (one dose twice a day 30 minutes before the meal) and the third group received no supplement at all.

The onset of normalization (in days) of the symptoms of gastroenteritis in all groups were recorded and are shown in Table 2 below.

TABLE 2

| | Onset of the normalization of the symptom, days | | |
|---|---|---|---|
| Symptoms | Food supplement | n | Control |
| Body temperature | 2.8 ± 0.2 | 2.7 ± 0.2 | 3.7 ± 0.2 |
| Intoxication | 2.5 ± 0.1 | 3.6 ± 0.1 | 4.6 ± 0.1 |
| Abdominal pain | 3.3 ± 0.2 | 5.1 ± 0.2 | 6.1 ± 0.2 |
| Diarrhea | 1.8 ± 0.2 | 3.4 ± 0.2 | 4.4 ± 0.2 |

Colibacterin (Colibacterinum siccum) is the freeze-dried preparation of live *E. coli* M-17 produced by BIOMED Ltd., Moscow, Russia, and recommended for use against diarrhea [Vidal Handbook: Pharmaceutical preparations in Russia (N. B. Nikolaeva, B. P. Alperovich and V. N. Sovinov, Eds.) AstraPharmService, 1997, Moscow, p. 275].

Example 9

Application of the food supplement (Example 4) in patients with acute GI infections

Patients with severe GI infections of various etiologies: salmonellosis, escherichiosis, shigellosis, staphylococcal infections and food intoxications of unknown etiology were included in the study. In all patients the hospitalization was indicated by an acute onset of the disease and appearance of acute gastroenteritis. The total of 186 patients were treated with the food supplement and a similar group of 102 patients received standard treatment.

The onset of normalization (in days) of the symptoms of gastroenteritis in all groups were recorded and are shown in Table 3 below.

TABLE 3

| | Onset of normalization, days | |
|---|---|---|
| Symptoms | Study group | Control |
| Fever | 1.2 ± 0.3 | 2.7 ± 0.3 |
| Weakness | 1.6 ± 0.2 | 2.9 ± 0.3 |
| Abdominal pain | 1.5 ± 0.2 | 2.4 ± 0.3 |
| Diarrhea | 2.3 ± 0.2 | 4.7 ± 0.4 |
| Days in bed | 4.8 ± 0.3 | 6.7 ± 0.4 |

In a separate study a group of 30 patients with intestinal typhoid was treated with the food supplement. In 80% of patients the symptoms of disease disappeared within 3 days. Only in 3 cases the supplement treatment was stopped due to the development of more severe chronic colitis.

Example 10

Applications of the food supplement (Example 4) in patients with GI disorders caused by antibiotics

Patients with severe GI disorders were divided in 2 groups. Group I contained 48 patients with peptic ulcer disease who developed GI disorders after antibiotic treatment against *H. pylori*. Group II contained 22 patients that developed GI disorders following antibiotic treatment of pneumonia.

The food supplement (5 ml) was given 3 times a day before meals for 7 days. In both groups symptoms of diarrhea disappeared in 2–3 days in all the patients. After the administration of the supplement, complete normalization of intestinal microflora was observed in 84.5% of the patients. It was demonstrated by a dramatic increase in lactobacilli and Bifidobacteria, reduction on the general count of E. coli, complete disappearance of the hemolytic E. coli and other pathogens such as Staphylococci, Proteus vulgaris and even Candida sps. In the remaining 15.5% of the patients, a significant improvement was observed.

Example 11

Application of the food supplement (Example 5) in patients with late radiation enterocolitis The food supplement (10 ml, 3 times a day for 14 days, 30 minutes before the meals) was given to 24 patients with womb, colon and gastric cancer that developed enterocolitis following radiation therapy or a combination of radiation and chemotherapy.

Prior to the use of the food supplement, all patients complained about frequent and painful desire to defecate, liquid stool (4–12 times a day) appearance of mucous (9 cases) and blood (3 cases) in the stool.

Two or three days after ingesting the supplement, all the patients noted the lessening of pain and reduction in the number of defecations; the stool had a normal appearance. Four to five days later the diarrhea syndrome was gone, the appearance of blood and mucus ceased. The blood analysis showed a strong improvement in blood indicators.

In the control group of a similar size the symptoms persisted.

Example 12

Application of the food supplement (Example 4) in AIDS patients

Patients suffering from AIDS frequently develop chronic diarrhea. A group of such patients was given 10 ml of the food supplement (Example 5) 3 times a day 30 minutes before the meals for 20 days. The control group received no supplement. The results of the treatment are shown in Table 4 below.

TABLE 4

| Parameter | Food supplement | Control |
| --- | --- | --- |
| No. of patients | 30 | 20 |
| Average age, years | 38 ± 1 | 36 ± 2 |
| Daily defecation frequency: | | |
| at the onset of the Exp. | 3.4 ± 0.3 | 3.6 ± 0.3 |
| at the end of the Exp. | 1.1 ± 0.1 | 3.2 ± 0.3 |
| one month after the Exp. | 1.5 ± 0.2 | 3.7 ± 0.3 |
| Av. onset of normalization | 6.0 ± 0.7 | remained abnormal |

Patients receiving the food supplement showed normalization of intestinal microflora: reduction in general number of coliforms, disappearance of the hemolytic E. coli increase in the numbers of Lactobacilli and Bifidobacteria, reduction in Candida sps.

Example 13

Application of the food/feed additive (Example 3) for accelerated weight increase in healthy piglets Healthy piglets were administered 3 ml per os of the food/feed additive per piglet per day until weaning. The group receiving the feed additive gained weight at weaning on the average 1.0 kg per piglet more than the control group.

Example 14

Application of the feed additive (Example 5) in healthy piglets

Several hundreds healthy piglets were administered 3 ml per os of the feed additive per piglet on the first and third day after delivery and at weaning. Mortality was cut down by 50% compared with the control group receiving standard prophylactic treatment with antibiotics. The group receiving the feed additive gained weight at weaning on the average 0.39 kg per piglet more than the control group. When the feed additive and antibiotic treatment were compared in the same litter, the weight gain in the piglets obtaining the feed additive was found higher by 2.4 kg than in the control.

Example 15

Application of the feed additive (Example 4) in piglets showing diarrhea

Several hundred piglets showing diarrhea were given daily 5 ml per os of the feed additive per piglet. The control group of the same size was treated with antibiotics: advocin, gentiamycin, amoxicillin. The symptoms of diarrhea in the group receiving the feed additive disappeared within 1–2 days. No mortality was observed, and piglets developed normally. Antibiotics stopped diarrhea in the great majority of piglets but the piglets remained stunted in their development.

About 70 retarded piglets, that received antibiotic treatment against diarrhea for a week, and generally considered lost, were given the feed additive for three days. All but two survived.

Example 16

Application of the feed additive (Example 4) in healthy calves

Day-old healthy calves were administered 5 ml of the feed additive a day in milk during 7 days. More than 95 % of the calves did not developed diarrhea until they were 14 days old, when a few cases positive for Rotavirus were diagnosed. Normally, the incidence of diarrhea in this farm is 20–30%.

Example 17

Application of the feed additive (Example 6) in calves showing diarrhea

Calves developing diarrhea were given daily 10 ml of the feed additive per animal with milk during 3–5 days. The symptoms of diarrhea disappeared within 1–2 days in 90–95% of calves. In the remaining 5–10% the diarrhea was caused by virus. These calves were treated with antibiotics with poor results.

Example 18

Application of the feed additive (Example 6) in healthy lambs and goat kids

Day-old healthy lambs and goat kids were administered 3 ml of the feed additive a day in milk during 7 days. In some cases slight to moderate signs of diarrhea were observed.

These signs usually disappeared spontaneously or were successfully treated with an increased dose of the feed additive (5 ml). Normally the insidence of diarrhea in these farms is 50% for baby lambs and for goat kids.

Example 19

Application of the feed additive (Example 5) in lambs and goat kids showing diarrhea The feed additive was tested in a herd suffering from pathogenic *E. coli* infections. In the year preceding the experiment, about 90 from 120 lambs and goat kids died from diarrhea. Treatment with antibiotics was ineffective, since the disease developed suddenly and with fast mortality. Lambs and goat kids developing diarrhea were given daily 5 ml of the feed additive per animal with milk during 3–5 days. A matching group of animals was treated, as normally recommended, with antibiotics. The symptoms of diarrhea disappeared within 1–2 days in about 90% of the lambs and goat kids receiving the feed additive. Their further development appeared normal. The control group receiving antibiotics (gentamycin) showed much poorer results. Diarrhea in this group persisted, calling for repeated treatment with antibiotics. The development of the control group was severely retarded.

Example 20

Application of the feed additive (Example 5) in poultry

The feed additive was added to the drinking water with the average uptake of 0.01 ml of the additive per day per chick during the breeding period (42–49 days). An increase of 3.2% in weight gain, accompanied by 4% improvement in food conversion was noted in controlled trials in broilers.

Excellent results were also obtained with turkeys of age 1 day to 6 weeks. Each bird received 0.01 ml of the additive per day. A weight gain of over 10% was observed, along with reduced mortality rate. Birds which still exhibited diarrhea, were treated with 0.1 ml per day of the food additive, without any treatment by antibiotics, and showed better recovery from the control birds which were treated with only antibiotics.

Example 21

Application of the feed additive (Example 5) in dogs and cats

Application of the feed additives in puppies resulted in cessation of the symptoms of diarrhea within 24–48 hours.

Example 22

Application of the feed additive (Example 5) in mice;

Evidence for immunostimulation

Two-weeks-old C571B1 mice were divided into 4 groups of 10 animals in each. Mice were deprived water from 4:00 pm to 8:00 am and then given 15 ml of either water (groups 1 & 3) or the feed additive (groups 2 & 4). This treatment was repeated for 2 weeks. At the end of this treatment mice from groups 3 and 4 were subjected to laparotomy under ether narcosis. A cut of 1.5 cm was made in the abdominal wall. Irritation of intestine was carried out by a dry gause. All the mice were sacrificed 24 hours after laparotomy; spleens were excised. Splenocytes were isolated and cultured on RPMI medium for 48–72 hours in the presence of phytohemagglutinin (PHA). In the group treated with the feed additive the proliferative activity of splenocytes reduced by laparotomy was recovered.

Splenocytes proliferation induced by PHA:

| | |
|---|---|
| 1. Control group/water | 3060 ± 290 |
| 2. Control group/water/laparotomy | 2120 ± 300 |
| 3. Test group/BioCocktail | 2740 ± 370 |
| 4. Test group/BioCocktail/laparotomy | 3040 ± 520 |

Example 23

Application of the food additive (Example 4) in human;

Evidence for immunostimulation

A number of patients were operated for malignant tumors of womb, cervix, stomach, and intestine. The gynecological patients (20 patients) received follow-up radiotherapy; the abdominal patients (30 patients) received chemotherapy. About half of the patients received the food additive twice daily for the duration of therapy. In all patients receiving the food additive there was observed a significant immunostimulation, as expressed in:

| | Gynecological tumors | | Abdominal tumors | |
|---|---|---|---|---|
| | Control | Food Additive | Control | Food Additive |
| T-lymphocytes (CD3+, HLA−, DR+) Lymphocyte blast transformation | 0.03 ± 0.01 | 0.10 ± 0.03 | 1.0 ± 0 1 | 1.6 ± 0.2 |
| a. spontaneous | 530 ± 110 | 880 ± 80 | 700 ± 120 | 1070 ± 100 |
| b. PHA-induced | 1600 ± 360 | 5720 ± 2100 | 4400 ± 1340 | 13370 ± 3720 |
| Phagocytes No (%) | 60.0 ± 2.9 | 76.5 ± 2.2 | 57.7 ± 1.5 | 74.2 ± 1.9 |

Example 24

Bacteria preservation effect of the formulation

*E. coli* cells were dispersed in a formulation prepared as described under Example 1 above and was maintained for 6 months at room temperature. Both at the beginning and at the end of the 6 months period, samples derived from the dispersion were seeded at appropriate consecutive dilutions on nutrient broth agar plates. The number of colony forming units was determined for both samples. The concentration determined was $1\times10^7$ in both cases, showing the effect of the formulation in preserving microorganisms. The above experiment was performed in parallel with Pseudomonas putida, yielding the same results.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A veterinary feed additive for accelerating animal weight gain, such that an animal receiving the feed additive gains more weight at a given time as compared with a controlled animal, the feed additive comprising at least one volatile fraction (VF) of a plant extract, wherein said plant extract is obtained by water extraction and said volatile fraction being prepared by steam distillation of said plant extract under a pressure lower than atmospheric pressure and at a bath temperature not exceeding 38° C.

2. The veterinary feed additive of claim 1, comprising distilled water and volatile fractions of beet, dill and grapefruit.

3. A food additive for accelerating weight gain in a recipient thereof, such that a recipient receiving the food additive gains more weight at a given time as compared with a controlled patient, the food additive comprising at least one volatile fraction (VF) of a plant extract, wherein said plant extract is obtained by water extraction and said volatile fraction being prepared by steam distillation of said plant extract under a pressure lower than atmospheric pressure and at a bath temperature not exceeding 38° C.

4. The food additive of claim 3, comprising distilled water and volatile fractions of beet, dill and parsley.

* * * * *